US010478476B2

(12) United States Patent
Haze et al.

(10) Patent No.: US 10,478,476 B2
(45) Date of Patent: Nov. 19, 2019

(54) USE OF FULL-LENGTH AMELOGENIN FOR PROMOTING NERVE GROWTH OR REGENERATION (71) Applicants: Hadasit Medical Research Services and Development Ltd., Jerusalem (IL); Yissum Research Development Company of the Hebrew University of Jerusalem Ltd., Jerusalem (IL)

(72) Inventors: Amir Haze, ModiIn (IL); Anat Blumenfeld, Mevaseret Zion (IL); Dan Deutsch, Motza Elite (IL)

(73) Assignees: Hadasit Medical Research Services and Development Ltd., Jerusalem (IL); Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 15/763,550

(22) PCT Filed: Sep. 29, 2016

(86) PCT No.: PCT/IL2016/051067
§ 371 (c)(1),
(2) Date: Mar. 27, 2018

(87) PCT Pub. No.: WO2017/056092
PCT Pub. Date: Apr. 6, 2017

(65) Prior Publication Data
US 2018/0271950 A1 Sep. 27, 2018

Related U.S. Application Data (60) Provisional application No. 62/234,714, filed on Sep. 30, 2015.

(51) Int. Cl.
A61K 38/00 (2006.01)
A61K 38/16 (2006.01)
A61K 38/28 (2006.01)
A61K 38/39 (2006.01)
A61K 38/18 (2006.01)
A61K 38/30 (2006.01)
A61K 45/06 (2006.01)

(52) U.S. Cl.
CPC ............ *A61K 38/39* (2013.01); *A61K 38/185* (2013.01); *A61K 38/1825* (2013.01); *A61K 38/1858* (2013.01); *A61K 38/30* (2013.01); *A61K 45/06* (2013.01); *Y02A 50/469* (2018.01)

(58) Field of Classification Search
None
See application file for complete search history.

(56) References Cited

U.S. PATENT DOCUMENTS

2011/0312891 A1 12/2011 Gestrelius et al.

FOREIGN PATENT DOCUMENTS

| WO | WO 01/34178 | 5/2001 |
| WO | WO 2006/134602 | 12/2006 |
| WO | WO 2011/077086 | 6/2011 |
| WO | WO 2012/153333 | 11/2012 |
| WO | WO 2017/056092 | 4/2017 |

OTHER PUBLICATIONS

International Search Report and the Written Opinion dated Feb. 6, 2017 From the International Searching Authority Re. Application No. PCT/IL2016/051067. (16 Pages).
Dadon-Nachum et al. "Differentiated Mesenchymal Stem Cells for Sciatic Nerve Injury", Stem Cell Reviews and Reports, XP019927865, 7(3): 664-671, Published Online Feb. 16, 2011. p. 665, col. 1, Para 2, p. 667, col. 1, Lines 4-24.
Deutsch et al. "Amelogenin, A Major Structural Protein in Mineralizing Enamel, is also Expressed in Soft Tissues: Brain and Cells of the Hematopoietic System", European Journal of Oral Sciences, 114(Suppl.1): 183-189, May 2006.
Gruenbaum-Cohen et al. "Amelogenin in Cranio-Facial Development: The Tooth as a Model to Study the Role of Amelogenin During Embryogenesis", Journal of Experimental Zoology, Part B: Molecular and Developmental Evolution, 312B(5): 445-457, Published Online Dec. 18, 2008.
Hanhan et al. "Skeletal Ligament Healing Using the Recombinant Human Amelogenin Protein", Journal of Cell and Molecular Medicine, 20(5): 815-824, Published Online Feb. 24, 2016.
Huang et al. "Effects of Human Full-Length Amelogenin on the Proliferation of Human Mesenchymal Stem cells Derived From Bone Marrow", Cell and Tissue Research, XP019860977, 342(2): 205-212, Published Online Oct. 22, 2010. Abstract.
Romanelli et al. "Amelogenin, An Extracellular Matrix Protein, in the Treatment of Venous Leg Ulcers and Other Hard-to-Heal Wounds: Experimental and Clinical Evidence", Clinical Interventions in Aging, XP002765917, 3(2): 263-272, Published Online Jun. 2008.
Sadan et al. "Migration of Neurotrophic Factors-Secreting Mesenchymal Stem Cells Toward a Quinolinic Acid Lesion as Viewed by Magnetic Resonance Imaging", Stem Cells, XP002545734, 26(10): 2542-2551, Published Online Jul. 17, 2008. Abstract, Conclusion, p. 2548, col. 1, Lines 10-13.

(Continued)

Primary Examiner — Olga N Chernyshev (57) ABSTRACT

A method of promoting nerve growth or regeneration in a subject in need thereof, wherein the subject is not afflicted with a substantial connective tissue damage, is provided. The method comprises administering to the subject a therapeutically effective amount of full-length amelogenin, thereby promoting nerve growth or regeneration in the subject.

21 Claims, 2 Drawing Sheets
Specification includes a Sequence Listing.

(56) References Cited

OTHER PUBLICATIONS

International Preliminary Report on Patentability dated Apr. 12, 2018 From the International Bureau of WIPO Re. Application No. PCT/IL2016/051067. (9 Pages).
Communication Pursuant to Article 94(3) EPC Dated Jul. 17, 2019 From the European Patent Office Re. Application No. 16791448.0. (4 Pages).

SEQUENCE LISTING

<160> NUMBER OF SEQ ID NOS: 1

<210> SEQ ID NO 1
<211> LENGTH: 175
<212> TYPE: PRT
<213> ORGANISM: Homo sapiens

<400> SEQUENCE: 1

Met Pro Leu Pro Pro His Pro Gly His Pro Gly Tyr Ile Asn Phe Ser
1               5                   10                  15

Tyr Glu Val Leu Thr Pro Leu Lys Trp Tyr Gln Ser Ile Arg Pro Pro
            20                  25                  30

Tyr Pro Ser Tyr Gly Tyr Glu Pro Met Gly Gly Trp Leu His His Gln
        35                  40                  45

```
Ile Ile Pro Val Leu Ser Gln Gln His Pro Pro Thr His Thr Leu Gln
    50              55                  60
Pro His His His Ile Pro Val Val Pro Ala Gln Gln Pro Val Ile Pro
65              70                  75                      80
Gln Gln Pro Met Met Pro Val Pro Gly Gln His Ser Met Thr Pro Ile
            85                  90                  95
Gln His His Gln Pro Asn Leu Pro Pro Pro Ala Gln Gln Pro Tyr Gln
            100             105             110
Pro Gln Pro Val Gln Pro Gln Pro His Gln Pro Met Gln Pro Gln Pro
        115             120             125
Pro Val His Pro Met Gln Pro Leu Pro Pro Gln Pro Pro Leu Pro Pro
    130             135             140
Met Phe Pro Met Gln Pro Leu Pro Pro Met Leu Pro Asp Leu Thr Leu
145             150             155             160
Glu Ala Trp Pro Ser Thr Asp Lys Thr Lys Arg Glu Glu Val Asp
                165             170             175
```

USE OF FULL-LENGTH AMELOGENIN FOR PROMOTING NERVE GROWTH OR REGENERATION

RELATED APPLICATIONS

This application is a National Phase of PCT Patent Application No. PCT/IL2016/051067 having International filing date of Sep. 29, 2016, which claims the benefit of priority under 35 USC § 119(e) of U.S. Provisional Patent Application No. 62/234,714 filed on Sep. 30, 2015. The contents of the above applications are all incorporated by reference as if fully set forth herein in their entirety.

SEQUENCE LISTING STATEMENT

The ASCII file, entitled 72563SequenceListing.txt, created on Mar. 27, 2018, comprising 1,994 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to methods of promoting nerve growth or regeneration.

Injury to the nervous system is often associated with permanent impairment. Though peripheral nerve has a high regenerative potential, spontaneous regeneration leading to recovery of function rarely occurs after nerve transection, and the outcome of therapeutic intervention as microsurgical suturing, autologous grafting and use of nerve conduits is usually incomplete [1]. The majority of peripheral nerve injuries occur in the upper limb and are due to traumatic causes. These injuries disproportionately afflict young healthy civilians and military officers who are at risk of traumatic injuries. Severe nerve injury has a devastating impact on a patients' quality of life. Typical symptoms are sensory and motor function defects that can result in complete paralysis of the affected limb or development of intractable neuropathic pain [2]. In peacetimes these injuries account for about 5% of all admitted traumas, but during wartimes their prevalence is much higher [3]. Peripheral nerves contain myelinated motor and sensory axons, as well as unmyelinated sensory and autonomic axons. As mentioned above, the neurons partially regenerate their axons after injury, and the Schwann cells within the denervated nerve pathways support the regenerating axons and remyelinate the large ones [1]. However, exon regeneration is a slow process, progressing at speeds of 1 and 3 mm/day in humans and animals, respectively [4]. In human patients the outcome of nerve regeneration varies widely, depending on the extent and severity of injury and the distance and time required for axons to regenerate. Hence, functional outcomes after nerve injuries are frequently disappointing. Lately, several reports describing different aspects of the beneficial role mesenchymal stem cells (MSC) have during peripheral nerve regeneration were published. Guo et al. [5] described the neurotropic paracrine effects of application of human MSCs to site of injured sciatic nerve. Wakao et al. [6] demonstrated that MSCs have the potential to differentiate into Schwann cells. Biological conduits (tube implants) and vein conduits lined with MSCs were shown to have better healing potential in animal models than the same conduits without MSC [7, 8].

Recombinant human amelogenin protein (rHAM+) was previously reported to support significant and progressive regeneration of the tooth-supporting (periodontal) tissues: alveolar bone, periodontal ligament and cementum (a thin mineralized layer covering the tooth root), through recruitment of MSC [10]. Additionally, fraction C of amelogenin has been implicated in neurogenesis (WO2011077086).

Additional background art includes: Deutsch et al. 2006 Eur. J. Oral. Sci. 114:183-189; Gruenbaum et al. 2009 J. Exp. Zool. 312B:445-457; WO2011077086; US20110312891; Hanhan et al., Journal of Cell Molecular Medicine, 2016, 20(5):815-24; and WO2012/153333.

SUMMARY OF THE INVENTION

According to an aspect of some embodiments of the present invention there is provided a method of promoting nerve growth or regeneration in a subject in need thereof, wherein the subject is not afflicted with a substantial connective tissue damage, the method comprising administering to the subject a therapeutically effective amount of full-length amelogenin, thereby promoting nerve growth or regeneration in the subject.

According to an aspect of some embodiments of the present invention there is provided a method of promoting nerve growth or regeneration, the method comprising contacting nervous tissue with an effective amount of full-length amelogenin, thereby promoting nerve growth or regeneration.

According to some embodiments of the invention, the nerve is of the peripheral nervous system (PNS).

According to some embodiments of the invention, the nerve is of the central nervous system (CNS).

According to some embodiments of the invention, the nerve growth or regeneration comprises nerve fiber outgrowth of a neuron, neural progenitor cell, or stem cell.

According to some embodiments of the invention, the neuron is the sciatic nerve. According to some embodiments of the invention, the subject suffers from a disease or condition selected from the group consisting of neuronal injury and a neurodegenerative disease.

According to some embodiments of the invention, the disease or condition is selected from the group consisting of traumatic brain injury, ischemic or hemorrhagic stroke, spinal cord injury, sciatic crush, Huntington's disease, Parkinson's disease, Alzheimer's disease, multiple system atrophy (MSA), spino-cerebellar atrophy, motor neuropathy, epilepsy or seizures, peripheral neuropathy, cerebral palsy, glaucoma, neurological injury resulting from exposure to a toxin, age related loss of neurons or neuronal connectivity and related deterioration of sensory, motor, reflect, or cognitive abilities, trigeminal neuralgia, glossopharyngeal neuralgia, Bell's Palsy, myasthenia gravis, muscular dystrophy, peripheral neuropathies caused by lead, dapsone, ticks, or *porphyria*, other peripheral myelin disorders, Gullain-Barre syndrome, ALS, Tourette's syndrome, central myelin disorders, neural paropathy, facial nerve crush and other trauma, chemotherapy and medication-induced neuropathies.

According to some embodiments of the invention, the disease or condition is an injury caused by or associated with a peripheral neuropathy and/or peripheral nerve damage associated with spinal cord injury.

According to some embodiments of the invention, the peripheral neuropathy is selected from the group consisting of diabetic neuropathy, virus-associated neuropathy, botulism-related neuropathy; toxic polyneuropathy, nutritional neuropathy, angiopathic neuropathy, sarcoid-associated neuropathy; carcinomatous neuropathy; compression neuropathy, and hereditary neuropathy.

According to some embodiments of the invention, the disease or condition is a neurological injury resulting from a trauma.

According to some embodiments of the invention, the trauma is optic nerve trauma or spinal cord trauma.

According to some embodiments of the invention, the subject is a mammal.

According to some embodiments of the invention, the subject is a human being.

According to some embodiments of the invention, the method further comprises administering to the subject a neurotrophic factor.

According to some embodiments of the invention, the method further comprises contacting the nervous tissue with a neurotrophic factor.

According to some embodiments of the invention, the neurotrophic factor is selected from nerve growth factor (NGF), insulin-like growth factor (IGF-1) and its active truncated derivatives such as gIGF-1 and Des(1-3)IGF-I, acidic and basic fibroblast growth factor (aFGF and bFGF, respectively), platelet-derived growth factors (PDGF), brain-derived neurotrophic factor (BDNF), ciliary neurotrophic factors (CNTF), glial cell line-derived neurotrophic factor (GDNF), neurotrophin-3 (NT-3), neurotrophin 4/5 (NT-4/5) and TGF-β1.

According to some embodiments of the invention, the amelogenin is human amelogenin.

According to some embodiments of the invention, the amelogenin is expressed from mesenchymal stem cells (MSCs) which have been genetically modified to express the same.

According to some embodiments of the invention, the amelogenin is comprised in a scaffold.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

The present invention, in some embodiments thereof, relates to methods of promoting nerve growth or regeneration.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Traumatic or combat induced peripheral nerve injuries are very common. Recovery of neural function depends on the severity of the injury. Following transection of the nerve, degenerative events, including the breakdown of axons and myelin, are initiated proximally and distally to the injury site. To restore the motor and sensory function regenerated nerve fibers must pass through the damaged area and re-establish connections with appropriate target organs. Although spontaneous axonal regeneration occurs, studies of clinical outcomes show severe functional deficits due to failure of connection or inappropriate connections. Thus, it is important to identify new approaches for repair after traumatic nerve injuries.

The present inventors have surprisingly discovered that ameloginin plays a role in nerve regeneration.

Figure 1A:
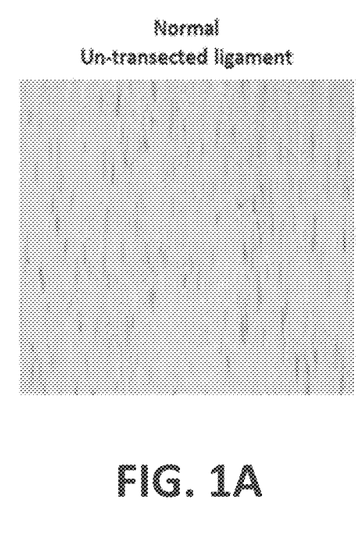
FIGS. 1A-C are photographs of an immunohistochemical analysis using a mouse monoclonal antibody against rat neurofilaments (brown staining) of un-transected ligaments (FIG. 1A), transected area 12 weeks after the operation of experimental ligament treated with 0.5 μg/μl rHAM$^+$ dissolved in PGA (FIG. 1C) and of control ligament treated with PGA carrier alone (FIG. 1B) in a rat MCL model.
Figure 1B:
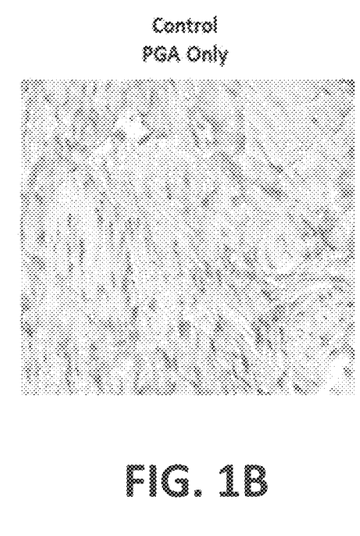
Figure 1C:
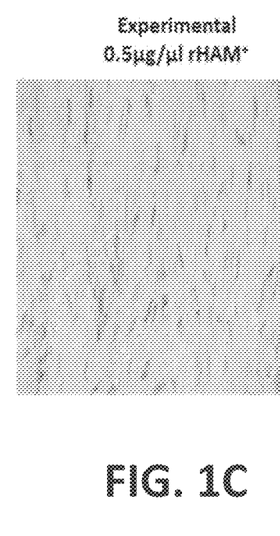

Using a knee medial collateral ligament (MCL) model, the present inventors showed that the proprioceptive free-nerve endings in the amelogenin-treated group were parallel to the collagen fibers similar to their arrangement in normal ligament, whilst in the control-transacted ligaments, the free nerve endings were entrapped in the scar tissue, lying in different directions, not parallel to the axis of the force (FIGS. 1A-C).

Whilst further reducing the present invention to practice, the present inventors used a rat sciatic nerve complete transection model to analyse the effect of amelogenin on nerve regeneration. In the experimental group, recombinant amelogenin was applied to the injured site. After 10 weeks, the present inventors noted that in the experimental group all six rats developed autotomy (FIGS. 2A-B), which is a known sign for sensory re-innervation, while in the control group none of the seven rats developed autotomy. Furthermore, rats in the experimental group could walk more stably and in a more coordinated fashion than the rats in the control group walk. In addition, the leg muscles of rats of the experimental group were less wasted than those in the control group.

Thus, according to one aspect of the present invention there is provided a method of promoting nerve growth or regeneration in a subject in need thereof, wherein the subject is not afflicted with a substantial connective tissue damage, the method comprising administering to the subject a therapeutically effective amount of full-length amelogenin, thereby promoting nerve growth or regeneration in the subject.

As used herein, the term "amelogenin" refers to any one of the alternatively spliced variants of the mammalian amelogenin polypeptide (e.g., human, rat, mouse amelogenin) which exhibits an amelogenin activity, e.g. enhancement of mesenchymal tissue regeneration.

The GenPept REFSEQ numbers for the 3 alternative protein isoforms of amelogenin are set forth in NP_001133.1, NP_872621.1, NP_872622.1.

The GenBank REFSEQ transcripts for amelogenin for the 3 human alternative transcripts are set forth in NM_001142.2, NM_182680.1 and NM_182681.1. Additional cDNA sequences (also including protein sequence) include: GenBank AF436849.1; BC069118.1; BC074951.2; M86932.1 and 567147.1.

Further details of the protein are further disclosed in Taylor et al., Protein expression and Purification 45 (2006), p. 43-53, the contents of which are incorporated herein by reference.

An amelogenin of the present invention also refers to homologs (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to any of the amelogenin sequences described above (for example that set forth in SEQ ID NO: 1) as determined using BlastP software of the National Center of Biotechnology Information (NCBI) using default parameters).

Full-length amelogenin refers to an amelogenin which comprises at least 150, 155, 160, 165 or 170 amino acids of the amelogenin amino acid sequence.

In some embodiments, the full-length amelogenin comprises 171 amino acids of the amelogenin amino acid sequence.

In some embodiments, the full-length amelogenin comprises 172 amino acids of the amelogenin amino acid sequence.

In some embodiments, the full-length amelogenin comprises 173 amino acids of the amelogenin amino acid sequence.

In some embodiments, the full-length amelogenin comprises 174 amino acids of the amelogenin amino acid sequence.

In some embodiments, the full-length amelogenin comprises 175 amino acids of the amelogenin amino acid sequence.

According to one embodiment, the amelogenin is a recombinant amelogenin.

To generate recombinant amelogenin the polynucleotide encoding the amelogenin polypeptide is inserted into an expression construct.

The expression construct preferably includes a polynucleotide sequence encoding the amelogenin under control of a transcriptional regulatory sequence (e.g. a promoter).

The phrase "an isolated polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

The expression construct can be generated using standard ligation and restriction techniques, which are well known in the art (see Maniatis et al., in: Molecular Cloning: A Laboratory Manual, Cold Spring Harbor Laboratory, New York, 1982). Isolated plasmids, DNA sequences, or synthesized oligonucleotides are cleaved, tailored, and religated in the form desired.

Promoters suitable for use with the present invention may be constitutive, tissue specific or regulatable (e.g. comprise response elements capable for directing transcription of the polynucleotide sequence so as to confer regulatable synthesis of the amelogenin).

Constitutive promoters suitable for use with some embodiments of the invention are promoter sequences which are active under most environmental conditions and most types of cells such as the cytomegalovirus (CMV) and Rous sarcoma virus (RSV).

A suitable response element for use in regulatable promoters can be, for example, a tetracycline response element (such as described by Gossen and Bujard (Proc. Natl. Acad. Sci. USA 89:5547-551, 1992); an ectysone-inducible response element (No D et al., Proc Natl Acad Sci USA. 93:3346-3351, 1996) a metal-ion response element such as described by Mayo et al. (Cell. 29:99-108, 1982); Brinster et al. (Nature 296:39-42, 1982) and Searle et al. (Mol. Cell. Biol. 5:1480-1489, 1985); a heat shock response element such as described by Nouer et al. (in: Heat Shock Response, ed. Nouer, L., CRC, Boca Raton, Fla., pp 167-220, 1991); or a hormone response element such as described by Lee et al. (Nature 294:228-232, 1981); Hynes et al. (Proc. Natl. Acad. Sci. USA 78:2038-2042, 1981); Klock et al. (Nature 329: 734-736, 1987); and Israel and Kaufman (Nucl. Acids Res. 17:2589-2604, 1989).

The expression construct of the present invention may also include one or more enhancers. Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

Polyadenylation sequences can also be added to the expression construct in order to increase the translation efficiency of the enzyme expressed from the expression construct of the present invention. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40.

In addition to the elements already described, the expression construct of the present invention may typically contain other specialized elements intended to increase the level of expression of cloned polynucleotides or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The expression construct may or may not include a eukaryotic replicon. If a eukaryotic replicon is present, then the vector is amplifiable in eukaryotic cells using the appropriate selectable marker. If the construct does not comprise a eukaryotic replicon, no episomal amplification is possible. Instead, the recombinant DNA integrates into the genome of the engineered cell, where the promoter directs expression of the desired polynucleotide.

Examples for mammalian expression constructs include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression constructs containing regulatory elements from eukaryotic viruses such as retroviruses can also be used by the present invention. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Viruses are specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I).

Recombinant viral vectors (e.g. adenoviruses or lenitviruses) are useful for in vivo expression of transgenic polynucleotides since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression construct of the present invention into mesenchymal stem cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al. [Biotechniques 4 (6): 504-512, 1986] and include, for example, stable or transient transfection, ultrasound, optical transfection, nucleofection, lipofection, electroporation and infection with recombinant viral vectors. In addition, see U.S. Pat. Nos. 5,464,764 and 5,487,992 for positive-negative selection methods.

Once transformed cells are generated, they may be tested (in culture) for their ability to express and synthesize amelogenin analyzed using standard chemical analytical methods such as, for example, HPLC, ELISA or GC-MS. Alternatively the cultures are comparatively analyzed for expression of the recombinant enzyme (e.g., amelogenin), using biochemical analytical methods such as immunoassays, Western blot and Real-time PCR.

A variety of prokaryotic or eukaryotic cells can be used as host-expression systems to express the amelogenin of the present invention. These include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

Preferably non-bacterial expression systems are used (e.g. mammalian expression systems such as CHO cells) to express the polypeptide of the present invention since it is preferred that the polypeptides of the present invention are glycosylated. In bacterial systems, a number of expression vectors can be advantageously selected. When large quantities of amelogenin are desired, vectors that direct the expression of high levels of the protein product, possibly as a fusion with a hydrophobic signal sequence, which directs the expressed product into the periplasm of the bacteria or the culture medium where the protein product is readily purified may be desired. Certain fusion protein engineered with a specific cleavage site to aid in recovery of the polypeptide may also be desirable. Such vectors adaptable to such manipulation include, but are not limited to, the pET series of *E. coli* expression vectors [Studier et al., Methods in Enzymol. 185:60-89 (1990)].

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

In cases where plant expression vectors are used, the expression of the polypeptide coding sequence can be driven by a number of promoters. For example, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] can be used. Alternatively, plant promoters can be used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

Various methods can be used to introduce the expression vector of the present invention into the host cell system. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Transformed cells are cultured under effective conditions, which allow for the expression of high amounts of recombinant polypeptide. Effective culture conditions include, but are not limited to, effective media, bioreactor, temperature, pH and oxygen conditions that permit protein production. An effective medium refers to any medium in which a cell is cultured to produce the recombinant polypeptide of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes and petri plates. Culturing can be carried out at a temperature, pH and oxygen content appropriate for a recombinant cell. Such culturing conditions are within the expertise of one of ordinary skill in the art.

Depending on the vector and host system used for production, the ameogenin of the present invention may either remain within the recombinant cell, secreted into the fermentation medium, secreted into a space between two cellular membranes, such as the periplasmic space in E. coli; or retained on the outer surface of a cell or viral membrane.

Following a predetermined time in culture, recovery of the amelogenin is effected.

The phrase "recovering the amelogenin" used herein refers to collecting the whole fermentation medium containing the amelogenin and need not imply additional steps of separation or purification.

Thus, amelogenins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

To facilitate recovery, the expressed coding sequence can be engineered to encode the amelogenin fused to a cleavable moiety. Such a fusion protein can be designed so that the polypeptide can be readily isolated by affinity chromatography; e.g., by immobilization on a column specific for the cleavable moiety. Where a cleavage site is engineered between the polypeptide and the cleavable moiety, the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

The amelogenin is preferably retrieved in "substantially pure" form.

As used herein, the phrase "substantially pure" refers to a purity that allows for the effective use of the amelogenin in the applications described herein.

In addition to being synthesizable in host cells, the amelogenin can also be synthesized using in vitro expression systems. These methods are well known in the art and the components of the system are commercially available.

As well as being provided in an isolated or pure form, the present inventors also consider cell therapy, whereby cells are genetically modified so as to express the amelogenin. Exemplary cells which may be transformed include mesenchymal stem cells.

The term "mesenchymal stem cell" or "MSC" is used interchangeably for adult cells which are not terminally differentiated, which can divide to yield cells that are either stem cells, or which, irreversibly differentiate to give rise to cells of a mesenchymal cell lineage e.g., adipose, osseous, cartilaginous, elastic and fibrous connective tissues, myoblasts, as well as to tissues other than those originating in the embryonic mesoderm (e.g., neural cells) depending upon various influences from bioactive factors such as cytokines.

MSC cultures utilized by some embodiments of the invention preferably include three groups of cells which are defined by their morphological features: small and agranular cells (referred to as RS-1, hereinbelow), small and granular cells (referred to as RS-2, hereinbelow) and large and moderately granular cells (referred to as mature MSCs, hereinbelow). The presence and concentration of such cells in culture can be assayed by identifying a presence or absence of various cell surface markers, by using, for example, immunofluorescence, in situ hybridization, and activity assays.

When MSCs are cultured under the culturing conditions of some embodiments of the invention they exhibit negative staining for the hematopoietic stem cell markers CD34, CD11B, CD43 and CD45. A small fraction of cells (less than 10%) are dimly positive for CD31 and/or CD38 markers.

According to a preferred embodiment of this aspect of the present invention, the mesenchymal stem cells are human.

According to another embodiment of this aspect of the present invention, the mesenchymal stem cells are isolated from newborn humans.

According to still another embodiment of this aspect of the present invention, the mesenchymal stem cells are autologous to the patient being treated.

According to still another embodiment of this aspect of the present invention, the mesenchymal stem cells are non-autologous (allergenic) to the patient being treated.

The mesenchymal stem cells may be derived from various tissues including but not limited to bone marrow, peripheral blood, placenta (e.g. fetal side of the placenta), cord blood, umbilical cord, amniotic fluid and from adipose tissue.

A method of enriching for mesenchymal stem cells from peripheral blood is described by Kassis et al [Bone Marrow Transplant. 2006 May; 37(10):967-76]. A method of isolating mesenchymal stem cells from placental tissue is described by Zhang et al [Chinese Medical Journal, 2004, 117 (6):882-887]. Methods of enriching for adipose tissue, placental and cord blood mesenchymal stem cells are described by Kern et al [Stem Cells, 2006; 24:1294-1301].

Bone marrow can be isolated from the iliac crest (or other bone) of an individual by aspiration. Low-density BM mononuclear cells (BMMNC) may be separated by a FICOL-PAQUE density gradient or by elimination of red blood cells using Hetastarch (hydroxyethyl starch). Preferably, mesenchymal stem cell cultures are generated by diluting BM aspirates (usually 20 ml) with equal volumes of Hank's balanced salt solution (HBSS; GIBCO Laboratories, Grand Island, N.Y., USA) and layering the diluted cells over about 10 ml of a Ficoll column (Ficoll-Paque; Pharmacia, Piscataway, N.J., USA). Following 30 minutes of centrifugation at 2,500×g, the mononuclear cell layer is removed from the interface and suspended in HBSS. Cells are then centrifuged at 1,500×g for 15 minutes and resuspended in a complete medium (MEM, α medium without deoxyribonucleotides or ribonucleotides; GIBCO); 20% fetal calf serum (FCS) derived from a lot selected for rapid growth of MSCs (Atlanta Biologicals, Norcross, Ga.); 100 units/ml penicillin (GIBCO), 100 µg/ml streptomycin (GIBCO); and 2 mM L-glutamine (GIBCO).

Adipose tissue-derived MSCs can be obtained by liposuction and mononuclear cells can be isolated manually by removal of the fat and fat cells, or using the Celution System (Cytori Therapeutics) following the same procedure as described above for preparation of MSCs.

Preferably the MSCs are at least 50% purified, more preferably at least 75% purified and even more preferably at least 90% purified.

Methods of purifying MSCs are known in the art and include for example culturing (in vitro or ex vivo) on polystyrene plastic surfaces (e.g. in a flask) by removing non-adherent cells (i.e. non-mesenchymal stem cells).

Other methods of selecting for MSCs are known in the art including for example positive selection against mesenchymal stem cell markers (e.g. CD105) and/or negative selection against hematopoietic stem and progenitor markers such as CD34, CD133, CD8, etc. Methods of determining protein cell-surface expression are well known in the art. Examples include immunological methods, such as, FACS analysis as well as biochemical methods (cell-surface labeling, e.g., radioactive, fluorescence, avidin-biotin).

Following isolation the cells are typically expanded by culturing in a proliferation medium capable of maintaining and/or expanding the isolated cells ex vivo. The proliferation medium may be DMEM, alpha-MEM or DMEM/F12. Preferably, the proliferation medium is DMEM. Preferably, the proliferation medium further comprises SPN, L-glutamine and a serum (such as fetal calf serum or horse serum).

As mentioned herein above, the amelogenin (either in its purified form or as cell therapy) is provided so as to promote nerve regeneration.

The phrase "promoting nerve regeneration" as used herein, refers to one or more of the following: increase in the rate of production of neuronal tissue, increase in the production of neuronal stem or progenitor cells, increase in nerve fiber outgrowth or neurons, improvement in the functionality of neuronal tissue, increase in the amount or quality of the neuronal tissue produced, increase in the length of neurons as compared to untreated control.

According to a specific embodiment, the amelogenin promotes nerve regeneration such that free nerve endings are parallel to collagen fibers in the connective tissue similar to their arrangement in normal ligament.

The present invention contemplates regeneration of nerves of the peripheral nervous system and/or the central nervous system.

According to an exemplary embodiment, the nerve is a sciatic nerve.

The subjects that are treated for nerve regeneration are typically mammalian subjects (e.g. humans). In one embodiment, the subjects are not inflicted with a substantial connective tissue damage (muscle, cartilage). Preferably, the subject does not have a connective tissue disorder such as lupus or arthritis. In one embodiment, the subject has suffered a trauma or wound (e.g. automobile accident, wounded during war, a home accident, a work accident). The trauma may include traumatic brain injury, stroke, spinal cord injury, sciatic crush, neural paropathy, facial nerve crush and other traumas.

According to a particular embodiment, the trauma is optic nerve trauma.

According to another embodiment, the trauma is a spinal cord trauma.

According to the above embodiments, it is contemplated that the subject may have been a healthy subject until the trauma or wound occurred.

In another embodiment, the subject is afflicted with a neuronal disease such as a neurodegenerative disease.

Exemplary neuronal diseases include, but are not limited to Huntington's disease, Parkinson's disease, Alzheimer's disease, multiple system atrophy (MSA), spino-cerebellar atrophy, motor neuropathy, epilepsy or seizures, peripheral neuropathy, cerebral palsy, glaucoma, neurological injury resulting from exposure to a toxin, age related loss of neurons or neuronal connectivity and related deterioration of sensory, motor, reflect, or cognitive abilities, trigeminal neuralgia, glossopharyngeal neuralgia, Bell's Palsy, myasthenia gravis, muscular dystrophy, peripheral neuropathies caused by lead, dapsone, ticks, or *porphyria*, other peripheral myelin disorders, Gullain-Barre syndrome, ALS, Tourette's syndrome, central myelin disorders, neural paropathy, facial nerve crush and other trauma, chemotherapy and medication-induced neuropathies.

The subject may have suffered an injury caused by, or associated with, a peripheral neuropathy and/or peripheral nerve damage associated with spinal cord injury.

Examples of peripheral neuropathies which may be treated according to methods of the present invention include diabetic neuropathy, virus-associated neuropathy, botulism-related neuropathy; toxic polyneuropathy, nutritional neuropathy, angiopathic neuropathy, sarcoid-associated neuropathy; carcinomatous neuropathy; compression neuropathy, and hereditary neuropathy.

In any of the methods described herein, the genetically modified MSCs (or the amelogenin alone) can be administered either per se or, preferably as a part of a pharmaceutical composition that further comprises a pharmaceutically acceptable carrier.

As used herein a "pharmaceutical composition" refers to a preparation of amelogenin or cells genetically engineered to express amelogenin, with other chemical components such as pharmaceutically suitable carriers and excipients. The purpose of a pharmaceutical composition is to facilitate administration of a compound to a subject.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol alginate, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

According to a preferred embodiment of the present invention, the pharmaceutical carrier is an aqueous solution of saline.

Techniques for formulation and administration of drugs may be found in "Remington's Pharmaceutical Sciences," Mack Publishing Co., Easton, Pa., latest edition, which is incorporated herein by reference.

Suitable routes of administration include direct administration at the site of injury (local administration) or into an area surrounding the nerves. In one embodiment, the amelogenin is applied to the transected axons of the nerve and/or to its surrounding sheaths.

In one embodiment, the amelogenin is administered into the brain or directly into and or around the spinal cord.

For any preparation used in the methods of the invention, the therapeutically effective amount or dose can be estimated initially from in vitro and cell culture assays. Preferably, a dose is formulated in an animal model to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals.

The data obtained from these in vitro and cell culture assays and animal studies can be used in formulating a range of dosage for use in human. For example an effective concentration of amelogenin was shown to be about 0.05-5 μg in rats.

The dosage may vary depending upon the dosage form employed and the route of administration utilized. The exact formulation, route of administration and dosage can be chosen by the individual physician in view of the patient's condition, (see e.g., Fingl, et al., 1975, in "The Pharmacological Basis of Therapeutics", Ch. 1 p. 1).

For injection, the active ingredients of the pharmaceutical composition may be formulated in aqueous solutions, preferably in physiologically compatible buffers such as Hank's solution, Ringer's solution, or physiological salt buffer.

Dosage amount and interval may be adjusted individually so that sufficient amount of amelogenin reach the appropriate cells. Dosages necessary to achieve the desired effect will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the individual being treated, the severity of the affliction, the manner of administration, the judgment of the prescribing physician, etc. The dosage and timing of administration will be responsive to a careful and continuous monitoring of the individual changing condition.

The protein and/or the engineered cells may be administered to the desired site by direct application either by an injection, by arthroscopic device or during open surgery. The cells may be placed in an isolated form, or placed in a suitable medium, or in a suitable matrix including scaffold matrixes that may incorporate the cells. The cells may be administered alone or together with other compounds intended to promote activity or proliferation of MSC, or with other compounds known to enhance regeneration and/or repair of these tissues.

Neurotrophic factors and/or neuropeptides may also be administered to the subject to enhance nerve growth and/or regeneration. These agents may be provided per se, or like the amelogenin may be expressed in cells such as mesenchymal stem cells.

In one embodiment, the mesenchymal stem cells are genetically modified to express amelogenin and are manipulated (e.g. by genetic modification or by using specific culturing protocols) to secrete neurotrophic factors.

In another embodiment, one population of mesenchymal stem cells are genetically modified to express amelogenin and another population of mesenchymal stem cells are manipulated (e.g. by genetic modification or by using specific culturing protocols) to secrete neurotrophic factors.

Protocols for differentiating human mesenchymal stem cells into neurotrophic factor secreting cells are known in the art—see for example WO 2006/134602 and WO 2009/144718.

As used herein, the phrase "neurotrophic factor" refers to a cell factor that acts on the central nervous system comprising growth, differentiation, functional maintenance and/or survival effects on neurons. Examples of neurotrophic factors include, but are not limited to, glial derived neurotrophic factor (GDNF), GenBank Accession Nos. L19063, L15306; brain-derived neurotrophic factor (BDNF), GenBank Accession No. CAA62632; neurotrophin-3 (NT-3); neurotrophin-4/5; Neurturin (NTN), GenBank Accession No. NP_004549; Neurotrophin-4, GenBank Accession No. M86528; Persephin, GenBank Accession No. AAC39640; brain derived neurotrophic factor, (BDNF), GenBank Accession No. CAA42761; artemin (ART), GenBank Accession No. AAD13110; ciliary neurotrophic factor (CNTF), GenBank Accession No. NP_000605; and Neublastin GenBank Accession No. AAD21075.

Since non-autologous cells are likely to induce an immune reaction when administered to the body several approaches have been developed to reduce the likelihood of rejection of non-autologous cells. These include either suppressing the recipient's immune system, providing anti-inflammatory treatment and/or encapsulating the non-autologous cells in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70: 479-83, Chang™ and Prakash S. Procedures for microencapsulation of enzymes, cells and genetically engineered microorganisms. Mol Biotechnol. 2001, 17: 249-60, and Lu M Z, et al., A novel cell encapsulation method using photosensitive poly(allylamine alpha-cyanocinnamylideneacetate). J Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 μm. Such microcapsules can be further encapsulated with additional 2-5 μm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Technol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 μm (Canaple L. et al., Improving cell encapsulation through size control. J Biomater Sci Polym Ed. 2002; 13:783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE™), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

It will be appreciated that as well as for in vivo use, the present inventors also contemplate promoting nerve growth ex vivo (e.g. in vitro) for example in a culture of cells. Thus, according to another aspect of the present invention there is provided a method of promoting nerve growth or regeneration, the method comprising contacting nervous tissue with an effective amount of full-length amelogenin.

Amelogenin of this aspect of the present invention has been described herein above.

Nervous tissue according to this aspect of the present invention includes but is not limited to neurons, axons and nerves sheaths.

The contacting is effected under conditions (i.e. for a length of time and under appropriate culturing conditions) such that nerve growth or regeneration occurs.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Use of Amelogenin for the Regeneration of Peripheral Nerve as Tested on Rat Sciatic Nerve Model Combat induced nerve injuries are common and may cause devastating loss of sensation, strength, and pain. Recovery is usually incomplete, leaving frustrating functional deficits. Based on preliminary data it is suggested that application of rHAM$^+$ may facilitate and improve peripheral nerve regeneration. Rat sciatic nerve are fully transected, rHAM$^+$ dissolved in its carrier is applied to the experimental groups and carrier alone to the control groups. The regenerative effect is evaluated by histological and functional tests 6 weeks following injury.

Example 1

Effect of Amelogenin on Nerve Tissue in Rat Fully Transected Knee Medial Collateral Ligament (MCL) Model The regeneration of the proprioceptive nerve endings after transection of the ligament was tested in a MCL rat model. 12 weeks after transection of the MCL, the proprioceptive free nerve endings in the experimental group, treated with 0.5 µg/µl rHAM$^+$, were parallel to the collagen fibers—similar to their arrangement in normal un-transected ligament. In control ligaments, treated only with the carrier of rHAM$^+$ propylene glycol alginate (PGA), the free nerve endings were entrapped in the scar tissue at different directions, not parallel to the axis of the force (FIGS. 1A-C).

Example 2

Effect of Amelogenin on Nerve Tissue in Rat Sciatic Nerve Transection Model

Methods:
The surgical procedure was performed according to Luria et al. [14, 15]. The right sciatic nerve of 8 week old Sabra female rats was operated. Rats were anaesthetized with an intra-peritoneal injection of ketamin and xylazin. Tramadol (SC), for analgesic was injected before the operation. The surgical site was shaved and washed with antiseptic solution before positioning for the surgery. Under dissecting microscope, the sciatic nerve on the right side was approached through a semi-tendinosus-biceps femoris (long head) muscle-splitting approach. The nerve was dissected free of surrounding connective tissue, and was transected sharply.

A. Initial Analysis. Transected nerves were repaired end-to-end using the 9-0 nylon suture. To the experimental group 7 µl of 1 µg/µl rHAM$^+$ dissolved in PGA is applied. To the control group 7 µl of PGA is applied. The wound was closed with 4-0 nylon sutures. The rats received pain relief medication (SC tramadol injections) twice a day for two days after the operation. Six weeks after transection, rats were evaluated for functional regeneration and then sacrificed for histological evaluation, by overdose injection of penthal and after the rat stopped breathing the chest is opened.

Results

Figure 2A:
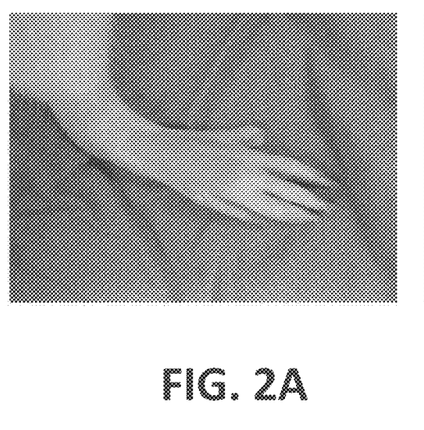
FIGS. 2A-B are photographs of the toes of rats (control—FIG. 2A, amelogenin treated—FIG. 2B) following sciatic nerve transection.
Figure 2B:
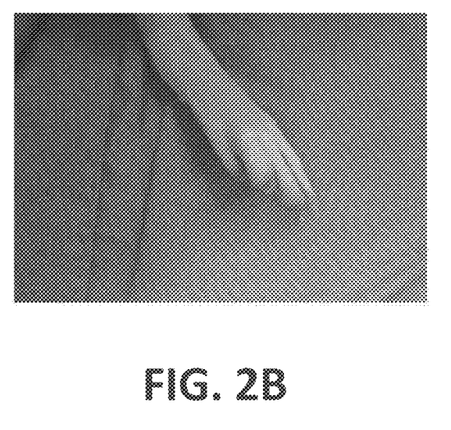

All rats in the experimental group appeared to walk better than the rats in the control group-treated with the PGA carrier alone. The walking of the experimental group appeared more coordinated with less falling as compared with the control group. All amelogenin-treated rats developed autotomy (leaking and chewing the tip of the toes), whilst none of the control rats developed the autotomy (FIGS. 2A-2B). Autotomy is related to re-innervation and return of sensation [21], Furthermore, the leg muscles of the experimental group appeared less wasted than the control group leg muscles and the toes are less contracted (FIGS. 2A-2B).

Additional Experiments that May be Performed to Analyze the Extent of Nerve Regeneration [4, 11, 14-16]:

Sciatic function index (SFI)/footprint analysis: Sciatic nerve injury paralyzes many muscles of the leg and foot, which affects walking and the rat foot print. Hence, footprint analysis is thought to be one of the most accurate methods for evaluation of sciatic nerve regeneration. Bain-Mackinnon-Hunter [18] described a formula, based on the rat ink footprint, which quantifies functional healing on a 0-(−100) scale.

Footprints are collected once weekly for quantitative, non-invasive evaluation of the integrated motor activity of the injured leg (as an indicator of nerve function). Measurements of print length (PL), 1st to 5th toe spread (TS) and 2nd to 4th intermediary toe spread (ITS) are taken. The rat hind legs are dipped in ink and then allowed to walk over a long sheet (42 cm/8.5 cm) of white paper along a narrow path into a dark chamber. The sheets are scanned and measurements of three consecutive prints are averaged, comparing control (normal side, N) to the injured side (the experimental side, E). The SFI is extrapolated using the Bain-Mackinnon-Hunter formula: SFI=−38.3((EPL−NPL)/NPL)+109.5((ETS−NTS)/NTS)+13.3((EITS−NITS)/NITS)−8.8. The SFI is a standardized index in which normal function is 0 and complete loss of function is −100.

Tibialis Anterior Muscle Weight: After sacrificing the rat, both left (untreated) and right (operated) leg muscles are harvested and weighed and the difference in weight between the injured and control legs is recorded. It is expected that innervated muscle will weigh more than the atrophied denervated muscle.

Histological Evaluation of Sciatic Nerve Regeneration and Axonal Count: The sciatic nerve is harvested 5 mm proximal and distal to the transection area. The nerves are fixed in 4% para-formaldehyde for 24 hours at 4° C., and incubated in 30% sucrose solution at 4° C. until the tissue is soaked in the tube. The tissues are then embedded in O.C.T compound, frozen at −80° C. and cryo-sectioned (8 μm thick). For morphological analysis, 3 slides are stained with hematoxylin and eosin (H&E) and 3 slides with toluidine blue. Axonal count is performed using immuno-fluorescence analysis with antibodies against (1) neurofilaments for detection of axons and (2) S100 for detection of Schwann cells. The O.C.T. compound is rinsed with PBS solution and incubated for two hours in 75 mM ammonium chloride to reduce the tissues auto-fluorescence. Slides are blocked using background buster (INNOVEX biosciences) for 30 minutes, followed by over-night incubation with the first antibody, at 4° C. in a humidified chamber. Following rinsing, slides are incubated for two hours with the secondary fluorescent antibody. Cell nuclei are counter-stained with 4',6-Diamidino-2-Phenylindole, Dihydrochloride (DAPI). Slides are examined by a confocal laser microscope. Quantification of the axons is performed using Image Pro Analyzer 7.0 software. The researcher is blind for the treatment the rat received.

Evaluation of Cellular and Molecular Processes Four Days after Sciatic Nerve Transection:

The amount of cells expressing the MSC markers CD105 and STRO-1 is tested using immuno-fluorescence reactions.

Real time quantitative PCR is performed to test changes in expression level of two sets of genes; I. Genes known to be involved in the initial stages of peripheral nerve regeneration [17]. (i) End target transcription factors of the CREB, C-JUN and ATF-3 pathways. (ii) up-stream genes of pathway(s) that its end-target gene was up-regulated. II. Genes known to play a role in regeneration of other tissues, including genes that are already detected changed in their expression in other in-vivo models, e.g. HIF1α, VEGF. Total RNA will be extracted from 6 experimental and 6 control sciatic nerves using the TRI-REAGENT standard protocol. Reverse transcription will be performed using Superscript RNase H-Reverse Transcriptase kit. Real-time qPCR is performed using Power SYBER Green PCR Master Mix on the Applied Biosystems 7300 real time PCR system. Expression level of all studied genes is normalized relative to the housekeeping gene Glyceraldehyde-3-phosphate-dehydrogenase (GAPDH).

Example 3

Use of Amelogenin for the Repair of Spinal Cord Injury as Tested on Rat Spinal Cord Contusion Model Rat Spinal Cord Model [18-20]

rHAM+ effects on the recovery from spinal cord injury is evaluated in a rat spinal cord contusion model. This model is the most acceptable and validated model, which closely mimics the common mechanism of injury in human.

The operation is performed on 8 weeks old Sabra female rats. Rats are anaesthetized with an intra-peritoneal injection of ketamin and xylazin. Tramadol (SC), for analgesic, is injected before the operation. The surgical site is shaved and washed with antiseptic solution before positioning for the surgery. Under dissecting microscope a laminectomy is performed at the level of the 9th thoracic vertebrae to expose a circle of dura mater. The contusion injuries are created by the NYU impactor; the exposed rat's spinal cord is impacted by dropping a bar 10 g in weight and 2.0 mm in diameter from a height of 10 cm. To the experimental groups (12 rats in each group) 7 μl of 0.25, 0.5 and 1 μg/μl rHAM$^+$ dissolved in PGA is applied. To the control group (12 rats) 7 μl of PGA is applied. The overlying muscles are closed using 4-0 vicryl sutures and the skin is closed using 5-0 nylon sutures. The rat receives pain relief medication (SC tramadol injections) twice a day for two days after the operation. Further post-operative treatments include saline (2.0 cm3, s. c.) for rehydration and Baytril (0.3 cm3, 22.7 mg/ml, s. c., twice daily) to prevent urinary tract infection and postoperative infections. Bladders are manually expressed twice daily until reflex bladder emptying returned.

Six weeks after the contusion injury, rats are evaluated for functional regeneration and then sacrificed for histological evaluation, by overdose injection of penthal and after the rat stopped breathing the chest is opened.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Muir, D., *The potentiation of peripheral nerve sheaths in regeneration and repair.* Exp Neurol, 2010. 223(1): p. 102-11.
2. Grinsell, D. and C. P. Keating, *Peripheral nerve reconstruction after injury: a review of clinical and experimental therapies.* Biomed Res Int, 2014. 2014: p. 698256.
3. Robinson, L. R., *Traumatic injury to peripheral nerves.* Muscle Nerve, 2000. 23(6): p. 863-73.
4. Wood, M. D., et al., *Outcome measures of peripheral nerve regeneration.* Ann Anat, 2011. 193(4): p. 321-33.
5. Guo, Z. Y., et al., *Human umbilical cord mesenchymal stem cells promote peripheral nerve repair via paracrine mechanisms.* Neural Regen Res, 2015. 10(4): p. 651-8.
6. Wakao, S., D. Matsuse, and M. Dezawa, *Mesenchymal stem cells as a source of Schwann cells: their anticipated use in peripheral nerve regeneration.* Cells Tissues Organs, 2014. 200(1): p. 31-41.
7. Wang, Y., et al., *Biological conduits combining bone marrow mesenchymal stem cells and extracellular matrix to treat long-segment sciatic nerve defects.* Neural Regen Res, 2015. 10(6): p. 965-71.
8. Carrier-Ruiz, A., et al., *Biological behavior of mesenchymal stem cells on poly-epsilon-caprolactone filaments and a strategy for tissue engineering of segments of the peripheral nerves.* Stem Cell Res Ther, 2015. 6(1): p. 128.
9. Taylor, A. L., et al., *High yield of biologically active recombinant human amelogenin using the baculovirus expression system.* Protein Expr Purif, 2006. 45(1): p. 43-53.
10. Haze, A., et al., *Regeneration of bone and periodontal ligament induced by recombinant amelogenin after periodontitis.* J Cell Mol Med, 2009. 13(6): p. 1110-24.
11. Kemp, S. W., et al., *Collagen nerve conduits promote enhanced axonal regeneration, schwann cell association, and neovascularization compared to silicone conduits.* Tissue Eng Part A, 2009. 15(8): p. 1975-88.
12. Deutsch, D., et al., *Amelogenin, a major structural protein in mineralizing enamel, is also expressed in soft tissues: brain and cells of the hematopoietic system.* Eur J Oral Sci, 2006. 114 Suppl 1: p. 183-9; discussion 201-2, 381.
13. Gruenbaum-Cohen, Y., et al., *Amelogenin in cranio facial development: the tooth as a model to study the role of amelogenin during embryogenesis.* J Exp Zool B Mol Dev Evol, 2009. 312B(5): p. 445-57.
14. Luria, S., et al., *Immune system augmentation by glatiramer acetate of peripheral nerve regeneration-crush versus transection models of rat sciatic nerve.* J Reconstr Microsurg, 2013. 29(8): p. 495-500.
15. Luria, S., et al., *Glatiramer acetate immune system augmentation for peripheral nerve regeneration in rat crushed sciatic nerve model.* J Bone Joint Surg Am, 2010. 92(2): p. 396-403.
16. Griffin, J. W., et al., *Measuring nerve regeneration in the mouse.* Exp Neurol, 2010. 223(1): p. 60-71.
17. Wu, D. and A. K. Murashov, *Molecular mechanisms of peripheral nerve regeneration: emerging roles of microRNAs.* Front Physiol, 2013. 4: p. 55.
18. Zhao, J., et al., *An Up-regulation of IRF-1 After a Spinal Cord Injury: Implications for Neuronal Apoptosis.* J Mol Neurosci, 2015.
19. Tang, L., et al., *Adipose-Derived Stem Cells Expressing the Neurogenin-2 Promote Functional Recovery After Spinal Cord Injury in Rat.* Cell Mol Neurobiol, 2015.
20. Duan, C., et al., *CDK14 Contributes to Reactive Gliosis via Interaction with Cyclin Y in Rat Model of Spinal Cord Injury.* J Mol Neurosci, 2015.
21. Lewin-Kowalik, J., et al., *Pre-degenerated peripheral nerve extracts applied to the proximal stump of transected sciatic nerve enhance both regeneration and autotomic behavior in rats.* Med Sci Monit, 2002. 8(10): p. Br414-20.

What is claimed is:

1. A method of promoting nerve growth or regeneration in a subject in need thereof, the method comprising directly administering to an injured nerve of the subject a therapeutically effective amount of full-length amelogenin, thereby promoting nerve growth or regeneration in the subject, wherein said injured nerve is a peripheral or a spinal cord nerve.

2. The method of claim 1, wherein the injured nerve is of the peripheral nervous system (PNS).

3. The method of claim 1, wherein the injured nerve is a spinal cord nerve.

4. The method of claim 1, wherein the nerve growth or regeneration comprises nerve fiber outgrowth of a neuron, neural progenitor cell, or stem cell.

5. The method of claim 1, wherein the injured nerve is the sciatic nerve.

6. The method of claim 1, wherein the subject suffers from a disease or condition selected from the group consisting of neuronal injury and a neurodegenerative disease.

7. The method of claim 6 wherein said subject suffers from a motor neuropathy or peripheral neuropathy.

8. The method of claim 6, wherein said disease or condition is an injury selected from the group consisting of spinal cord injury, sciatic crush and facial nerve crush.

9. The method of claim 7, wherein said peripheral neuropathy is selected from the group consisting of diabetic neuropathy, virus-associated neuropathy, botulism-related neuropathy; toxic polyneuropathy, nutritional neuropathy, angiopathic neuropathy, sarcoid-associated neuropathy; carcinomatous neuropathy; compression neuropathy, and hereditary neuropathy.

10. The method of claim 6, wherein said disease or condition is a neurological injury resulting from a trauma.

11. The method of claim 10, wherein said trauma is optic nerve trauma or spinal cord trauma.

12. The method of claim 1, wherein said subject is a mammal.

13. The method of claim 1, wherein said subject is a human being.

14. The method of claim 1, further comprising administering to the subject a neurotrophic factor.

15. The method of claim 14, wherein said neurotrophic factor is selected from nerve growth factor (NGF), insulin-like growth factor (IGF-1), acidic and basic fibroblast growth factor (aFGF and bFGF, respectively), platelet-derived growth factors (PDGF), brain-derived neurotrophic factor (BDNF), ciliary neurotrophic factors (CNTF), glial cell line-derived neurotrophic factor (GDNF), neurotrophin-3(NT-3) and neurotrophin 4/5 (NT-4/5).

16. The method of claim 1, wherein said amelogenin is human amelogenin.

17. The method of claim 1, wherein said amelogenin is a recombinant amelogenin expressed from genetically modified cells.

18. The method of claim 1, wherein said amelogenin is comprised in a scaffold.

19. The method of claim 15, wherein said insulin-like growth factor (IGF-1) comprises active truncated derivatives thereof selected from the group consisting of gIGF-1 and Des(1-3) IGF-I.

20. The method of claim 16, wherein said amelogenin is purified amelogenin.

21. The method of claim 1, wherein said amelogenin is applied directly to a transected axon of said injured nerve.

* * * * *